US012688940B2

(12) United States Patent (10) Patent No.: US 12,688,940 B2
Lee et al. (45) Date of Patent: Jul. 21, 2026

(54) OPTIMIZATION SYSTEM AND METHOD OF AI ALGORITHM FOR PREDICTION CORONARY ARTERY LESIONS BASED ON FFR

(71) Applicant: INDUSTRY-ACADEMIC COOPERATION FOUNDATION, YONSEI UNIVERSITY, Seoul (KR)

(72) Inventors: Joon Sang Lee, Seoul (KR); Hyeong Jun Lee, Seoul (KR); Young Woo Kim, Goyang-si (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 913 days.

(21) Appl. No.: 17/820,819

(22) Filed: Aug. 18, 2022

(65) Prior Publication Data

US 2023/0317297 A1 Oct. 5, 2023

(30) Foreign Application Priority Data

Mar. 10, 2022 (KR) ........................ 10-2022-0030019

(51) Int. Cl.
| | |
|---|---|
| *A61B 5/0215* | (2006.01) |
| *A61B 5/00* | (2006.01) |
| *A61B 5/026* | (2006.01) |
| *A61B 5/029* | (2006.01) |
| *A61B 6/50* | (2024.01) |
| *G06N 3/084* | (2023.01) |
| *G06N 5/04* | (2023.01) |
| *G06N 20/10* | (2019.01) |
| *G16H 30/40* | (2018.01) |

(Continued)

(52) U.S. Cl.
CPC .............. *G16H 50/50* (2018.01); *A61B 6/50* (2013.01); *A61B 6/504* (2013.01); *A61B 5/02007* (2013.01)

(58) Field of Classification Search
None
See application file for complete search history.

(56) References Cited

U.S. PATENT DOCUMENTS

2008/0285804 A1* 11/2008 Sefton .................... G06V 20/52
382/105
2016/0117819 A1* 4/2016 Taylor ................ A61B 5/02007
(Continued)

FOREIGN PATENT DOCUMENTS

CN 114386466 A * 4/2022 ....... G06F 18/23213
EP 4131154 A1 * 2/2023 ............ A61B 6/032
(Continued)

OTHER PUBLICATIONS

Office Action issued in corresponding Korean Patent Application No. 10-2022-0030019 mailed Dec. 9, 2024, in 8 pages.
(Continued)

*Primary Examiner* — Mohammed Rachedine
(74) *Attorney, Agent, or Firm* — BROADVIEW IP LAW, PC

(57) ABSTRACT

The present disclosure relates to an optimization system and method of an artificial intelligence (AI) algorithm for predicting a lesion in a coronary artery based on a fractional flow reserve (FFR), and more particularly, to a technology capable of providing an AI algorithm of which prediction accuracy of an FFR is improved.

14 Claims, 9 Drawing Sheets

(51) Int. Cl.
 _G16H 50/00_ (2018.01)
 _G16H 50/50_ (2018.01)
 _A61B 5/02_ (2006.01)

(56) References Cited

U.S. PATENT DOCUMENTS

| | | | |
|---|---|---|---|
| 2021/0290077 A1* | 9/2021 | Lee ...................... | A61B 5/1075 |
| 2022/0028069 A1* | 1/2022 | Aoyama ............... | G06T 7/0012 |
| 2022/0082647 A1* | 3/2022 | Sharma ................ | G06N 3/0895 |
| 2023/0142152 A1* | 5/2023 | Venugopal ........... | G06T 7/0016 |
| | | | 378/62 |

FOREIGN PATENT DOCUMENTS

| | | | | |
|---|---|---|---|---|
| KR | 10-2018-0008134 A | 1/2018 | | |
| KR | 102190431 B1 * | 12/2020 | ............ | A61B 6/507 |
| KR | 10-2251807 B1 | 5/2021 | | |
| KR | 102304402 B1 * | 9/2021 | ............ | G16C 20/90 |
| KR | 10-2328990 B1 | 11/2021 | | |
| WO | WO 2021/107607 A1 | 6/2021 | | |

OTHER PUBLICATIONS

Lee et al., "Optimization of Artificial Intelligence Algorithms for FFR Prediction in Gray Zone", ICMTE 2022, May 23, 2022.

Cha et al., "Optical coherence tomography-based machine learning for predicting fractional flow reserve in intermediate coronary stenosis: a feasibility study", Scientific Reports, (Nov. 24, 2020), 10:20421, https://doi.org/10.1038/s41598-020-77507-y.

Lee et al., "Optimization of Artificial Intelligence Algorithms for FFR Prediction in Gray Zone", Session I, pp. 17-18, Dec. 11, 2021.

\* cited by examiner

FIG. 5

| Algorithms | | $k = 3$ | $k = 4$ | $k = 5$ | $k = 6$ | $k = 7$ |
|---|---|---|---|---|---|---|
| Artificial Neural Network | MAE | 0.0407 ± 0.0118 | 0.0418 ± 0.0152 | 0.0414 ± 0.0170 | 0.0407 ± 0.0112 | 0.0366 ± 0.0161 |
| | $R^2$ score | 0.5446 ± 0.1182 | 0.4767 ± 0.1578 | 0.5212 ± 0.197 | 0.5719 ± 0.1080 | 0.5091 ± 0.3430 |
| Multilayer Perceptron | MAE | 0.0447 ± 0.0118 | 0.0367 ± 0.0141 | 0.0430 ± 0.0209 | 0.0407 ± 0.0198 | 0.0414 ± 0.0188 |
| | $R^2$ score | 0.3921 ± 0.2030 | 0.5241 ± 0.2514 | 0.4231 ± 0.317 | 0.5138 ± 0.2973 | 0.4442 ± 0.2315 |
| Random Forest | MAE | 0.0417 ± 0.0103 | 0.0497 ± 0.0148 | 0.0417 ± 0.0154 | 0.0429 ± 0.0140 | 0.0413 ± 0.0164 |
| | $R^2$ score | 0.5638 ± 0.0320 | 0.4555 ± 0.2122 | 0.5144 ± 0.205 | 0.5101 ± 0.1313 | 0.4872 ± 0.2272 |
| AdaBoost | MAE | 0.0432 ± 0.0102 | 0.0469 ± 0.0173 | 0.0456 ± 0.0186 | 0.0457 ± 0.0163 | 0.0441 ± 0.0155 |
| | $R^2$ score | 0.5428 ± 0.0301 | 0.4088 ± 0.2020 | 0.4601 ± 0.227 | 0.3792 ± 0.3117 | 0.3997 ± 0.2694 |
| Support Vector Machine | MAE | 0.0576 ± 0.0187 | 0.0579 ± 0.0229 | 0.0573 ± 0.0231 | 0.0562 ± 0.0212 | 0.0555 ± 0.0222 |
| | $R^2$ score | 0.2153 ± 0.1959 | 0.1981 ± 0.1895 | 0.2162 ± 0.265 | 0.1779 ± 0.3025 | 0.0779 ± 0.4303 |
| Gradient Boosting | MAE | 0.0406 ± 0.0082 | 0.0438 ± 0.0167 | 0.0431 ± 0.0171 | 0.0418 ± 0.0169 | 0.0409 ± 0.0166 |
| | $R^2$ score | 0.5852 ± 0.0405 | 0.4948 ± 0.1160 | 0.5152 ± 0.167 | 0.5028 ± 0.2148 | 0.4809 ± 0.2799 |
| Gaussian Process | MAE | 0.0540 ± 0.0179 | 0.0484 ± 0.0145 | 0.0412 ± 0.0250 | 0.0507 ± 0.0180 | 0.0436 ± 0.0153 |
| | $R^2$ score | 0.4927 ± 0.2498 | 0.5187 ± 0.2960 | 0.4967 ± 0.3168 | 0.4794 ± 0.2612 | 0.5317 ± 0.2541 |
| K-Nearest Neighbors | MAE | 0.0548 ± 0.0139 | 0.0492 ± 0.0204 | 0.0513 ± 0.0231 | 0.0500 ± 0.0220 | 0.0509 ± 0.0236 |
| | $R^2$ score | 0.2425 ± 0.1187 | 0.2898 ± 0.2536 | 0.2693 ± 0.317 | 0.2912 ± 0.2940 | 0.2251 ± 0.4227 |

FIG. 6

| Algorithms | MAE | MAE difference | $R^2$ score | $R^2$ score difference |
|---|---|---|---|---|
| Artificial Neural Network | 0.0414 ± 0.0170 | -0.0333 | 0.521 ± 0.197 | 0.338 |
| Multilayer Perceptron | 0.0430 ± 0.0209 | -0.0222 | 0.423 ± 0.317 | 0.062 |
| Random Forest | 0.0417 ± 0.0154 | -0.0156 | 0.514 ± 0.205 | 0.052 |
| AdaBoost | 0.0456 ± 0.0186 | -0.0161 | 0.460 ± 0.227 | 0.039 |
| Support Vector Machine | 0.0573 ± 0.0231 | -0.0101 | 0.216 ± 0.263 | -0.11 |
| Gradient Boosting | 0.0431 ± 0.0171 | -0.0148 | 0.515 ± 0.167 | 0.107 |
| Gaussian Process | 0.0412 ± 0.0250 | -0.0408 | 0.467 ± 0.440 | 0.438 |
| K-Nearest Neighbors | 0.0513 ± 0.0231 | -0.0164 | 0.269 ± 0.317 | -0.093 |

FIG. 8

| Algorithms | Gray zone accuracy [%] | Gray zone FFR accuracy percentage [%] | Expanded gray zone accuracy [%] | Expanded zone FFR accuracy percentage [%] |
|---|---|---|---|---|
| Artificial Neural Network k=6 | 55.9 (19/34) | 98.3 | 81.3 (52/64) | 94.1 |
| Multilayer Perceptron k=4 | 44.1 (15/34) | 98.9 | 76.6 (49/64) | 93.8 |
| Random Forest k=7 | 67.6 (23/34) | 98.3 | 85.9 (55/64) | 95.3 |
| AdaBoost k=5 | 67.6 (23/34) | 97.7 | 87.5 (56/64) | 94.9 |
| Support Vector Machine k=7 | 67.6 (23/34) | 98.1 | 92.2 (59/64) | 93.5 |
| Gradient Boosting k=5 | 58.8 (20/34) | 98.5 | 85.9 (55/64) | 94.2 |
| Gaussian Process k=7 | 52.9 (18/34) | 98.6 | 75.0 (48/64) | 96.1 |
| K-Nearest Neighbors k=5 | 64.7 (22/34) | 98.4 | 95.3 (61/64) | 91.6 |

OPTIMIZATION SYSTEM AND METHOD OF AI ALGORITHM FOR PREDICTION CORONARY ARTERY LESIONS BASED ON FFR

CROSS-REFERENCE TO RELATED APPLICATIONS

This application claims priority under 35 U.S.C. § 119 to Korean Patent Application No. 10-2022-0030019, filed on Mar. 10, 2022, in the Korean Intellectual Property Office, the disclosure of which is incorporated herein by reference in its entirety.

TECHNICAL FIELD

The present disclosure relates to an optimization system and method of an artificial intelligence (AI) algorithm for predicting a lesion in a coronary artery based on a fractional flow reserve (FFR), and more particularly, to an optimization system and method of an AI algorithm for predicting a lesion in a coronary artery based on an FFR capable of performing optimization of the AI algorithm so as to accurately predicting the FFR that may diagnose whether or not there is a lesion of the coronary artery with high reliability.

BACKGROUND

The coronary arteries are main blood vessels that supply blood to the myocardial tissue of the heart. The coronary arteries have limited blood supply due to stenosis in the blood vessels generated by arteriosclerosis or the like, and may ultimately cause serious symptoms such as myocardial infarction.

Therefore, as a standard method for diagnosing and treating vascular diseases, invasive X-ray angiography has been used, and in detail, a contrast agent is injected into a coronary artery of a patient, and X-rays are irradiated to examine a degree of stenosis that has occurred in the blood vessel.

However, since the degree of the stenosis of the coronary artery and myocardial ischemia are not proportional to each other, in other words, since there is a case where the stenosis does not affect an actual blood flow and thus, does not cause the myocardium ischemia even though the degree of the stenosis in a captured image is severe, it is difficult to determine ischemia occurring in the myocardium only by the degree of the stenosis measured from two-dimensional angiography such as X-ray angiography.

Accordingly, recently, it has been determined whether or not to perform a medical procedure by evaluating a pressure according to a blow flow in the coronary artery using a fractional flow reserve (FFR) in order to more accurately determine myocardial ischemia (lesion) due to the stenosis of the coronary artery.

Korean Patent No. 10-2251807 (entitled "Hyperparameter Optimization Algorithm Recommendation Method and Optimization Algorithm Recommendation System") discloses the related technology.

The disclosure of this section is to provide background information relating to the present disclosure. Applicant does not admit that any information contained in this section constitutes prior art.

SUMMARY

Embodiments of the present disclosure provide an optimization system and method of an artificial intelligence (AI)

algorithm for predicting a lesion in a coronary artery based on a fractional flow reserve (FFR) capable of performing optimization of the AI algorithm so as to improve accuracy of estimation of an FFR for predicting the lesion of the coronary artery, in particular, so as to further improve accuracy of estimation and reliability of an estimate of an FFR corresponding to a gray zone.

In one general aspect, an optimization system of an AI algorithm for predicting a lesion in a coronary artery based on an FFR includes: a data collection unit 100 collecting preset factor data in order to predict an FFR numerical value; a data processing unit 200 analyzing a correlation between the factor data collected by the data collection unit 100 and eliminating specific factor data; and an AI optimization analysis unit 300 performing learning processing using the factor data from which the specific factor data have been eliminated by the data processing unit 200 using a plurality of pre-stored AI algorithms, analyzing a learning result, and performing optimization processing of each AI algorithm based on an analysis result.

The data collection unit 100 may include: a biometric collection unit 110 receiving biometric factor data for each patient from the outside; a shape collection unit 120 receiving blood vessel shape factor data generated based on medical image data for each patient from the outside; and a flow generation unit 130 generating flow factor data for a cardiovascular region for each patient using the blood vessel shape factor data received by the shape collection unit 120, and the data collection unit 100 may receive an FFR value measured or predicted for each patient from the outside.

The flow generation unit 130 may include: a flow database (DB) unit 131 generating a plurality of virtual blood vessel models in advance, performing a computational fluid dynamics (CFD) simulation for the generated virtual blood vessel models, and constructing a database of CFD simulation performing result data for each virtual blood vessel model to store and manage the CFD simulation performing result data; and a flow extraction unit 132 deriving performing result data corresponding to the blood vessel shape factor data by the shape collection unit 120 based on the data stored and managed by the flow DB unit 131 and generating the performing result data as the flow factor data.

The data processing unit 200 may include: a DB construction unit 210 constructing a database of the biometric factor data, the blood vessel shape factor data, and the flow factor data by the data collection unit 100 for each patient; a correlation analysis unit 220 analyzing a correlation between each detailed factor data constituting all factor data by the DB construction unit 210 and the received FFR by applying a pre-stored technique; a factor elimination unit 230 selecting specific detailed factor data of which a correlation is a predetermined reference or less based on an analysis result of the correlation analysis unit 220 by applying a pre-stored technique and eliminating all factor data of a corresponding patient including the specific detailed factor data; and a DB reconstruction unit 240 correcting and reconstructing the database by the DB construction unit 210 based on an elimination result by the factor elimination unit 230.

The AI optimization analysis unit 300 may include: a first learning processing unit 310 performing learning processing by inputting the database by the DB reconstruction unit 240 as training data to a plurality of pre-stored heterogeneous AI algorithms; and a first optimization analysis unit 320 receiving an FFR prediction result using a learning result model for each AI algorithm by the first learning processing unit 310 and analyzing prediction result accuracy for each learning result model, the first learning processing unit 310 may divide all data included in the database by the DB reconstruction unit 240 into training data and test data according to a plurality of predetermined ratios by applying a pre-stored technique, and then input each training data to each AI algorithm to perform learning processing, and the first optimization analysis unit 320 may analyze accuracy of an FFR prediction result output from each learning result model using the test data by the first learning processing unit 310 and the received FFR.

The first optimization analysis unit 320 may analyze the accuracy of the FFR prediction result output from each learning result model to derive a specific ratio having the highest FFR prediction accuracy for each AI algorithm.

The AI optimization analysis unit 300 may further include: a second learning processing unit 330 controlling a weight for a hyper parameter that determines a property for each of a plurality of pre-stored heterogeneous AI algorithms by applying a pre-stored technique and inputting the training data divided according to the specific ratio having the highest FFR prediction accuracy derived by the first optimization analysis unit 320 to each controlled AI algorithm to perform learning processing; and a second optimization analysis unit 340 receiving an FFR prediction result for each learning result model by the second learning processing unit 330 using the test data divided according to the specific ratio having the highest FFR prediction accuracy derived by the first optimization analysis unit 320 and the received FFR and analyzing prediction result accuracy for each learning result model, and the second learning processing unit 330 may control weights for corresponding hyper parameters for each AI algorithm plural times under different conditions, and repeatedly perform learning processing for each controlled AI algorithm.

The second optimization analysis unit 340 may extract a learning result model having the highest FFR prediction accuracy for each AI algorithm, and analyze a weight control condition of a hyper parameter for the corresponding learning result model.

In another general aspect, an optimization method of an AI algorithm for predicting a lesion in a coronary artery based on an FFR that uses an optimization system of an AI algorithm for predicting a lesion in a coronary artery based on an FFR in which each step is performed by an arithmetic processing means including a computer includes: a data collection step (S100) of collecting preset factor data in order to predict an FFR numerical value, by a data collection unit; a data processing step (S200) of analyzing a correlation between the factor data collected by the data collection step (S100) and eliminating specific factor data, by a data processing unit; and an optimization analysis step (S300) of inputting the factor data from which the specific factor data have been eliminated by the data processing step (S200) to a plurality of pre-stored AI algorithms to perform learning processing, analyzing learning result, and performing optimization processing of each AI algorithm based on an analysis result, by an AI optimization analysis unit.

The data collection step (S100) may include: an input step (S110) of receiving biometric factor data, blood vessel shape factor data, and a measured or predicted FFR value for each patient; and a generation step (S120) of generating flow factor data for a cardiovascular region for each patient using the blood vessel shape factor data.

The generation step (S120) may include: a flow DB generation step (S121) of generating a plurality of virtual blood vessel models in advance, performing a CFD simulation for the generated virtual blood vessel models, and constructing a database of CFD simulation performing result data for each virtual blood vessel model to store and manage the CFD simulation performing result data; and a flow extraction step (S122) of deriving CFD simulation performing result data corresponding to the blood vessel shape factor data based on the data by the flow generation step and generating the CFD simulation performing result data as the flow factor data.

The data processing step (S200) may include: an initial DB construction step (S210) of constructing a database of the factor data by the data collection step (S100) for each patient; a correlation analysis step (S220) of analyzing a correlation between each detailed factor data constituting all factor data by the initial DB construction step (S210) and the received FFR by applying a pre-stored technique; a factor elimination step (S230) of selecting specific detailed factor data of which a correlation is a predetermined reference or less based on an analysis result of the correlation analysis step (S220) by applying a pre-stored technique and eliminating all factor data of a corresponding patient including the specific detailed factor data; and a final DB construction step (S240) of correcting the initial DB and reconstructing the database by construction step (S210) based on an elimination result by the factor elimination step (S230).

The optimization analysis step (S300) may include: a first learning processing step (S310) of performing learning processing by inputting the database by the final DB construction step (S240) as training data to a plurality of pre-stored heterogeneous AI algorithms, and dividing all data included in the database by the final DB construction step (S240) into training data and test data according to a plurality of predetermined ratios by applying a pre-stored technique and then inputting each training data to each AI algorithm; and a first optimization analysis step (S320) of receiving an FFR prediction result for each learning result model by the first learning processing step (S310) using each test data by the first learning processing step (S310) and the received FFR and analyzing accuracy of each learning result model based on the FFR prediction result, and in the first optimization analysis step (S320), a specific ratio having the highest FFR prediction accuracy may be derived for each AI algorithm.

The optimization analysis step (S300) may further include: second learning processing step (S330) of controlling weights for hyper parameters that determine a property for each of a plurality of pre-stored heterogeneous AI algorithms plural times under different conditions by applying a pre-stored technique and inputting the training data divided according to the specific ratio having the highest FFR prediction accuracy derived by the first optimization analysis step (S320) to each controlled AI algorithm to perform learning processing; and a second optimization analysis step (S340) of receiving an FFR prediction result for each learning result model by the second learning processing step (S330) using the test data divided according to the specific ratio having the highest FFR prediction accuracy derived by the first optimization analysis step (S320) and the received FFR and analyzing accuracy of each learning result model based on the FFR prediction result, and in the second optimization analysis step (S340), a learning result model having the highest FFR prediction accuracy for each AI algorithm may be extracted, and a weight control condition of a hyper parameter for the corresponding learning result model may be analyzed.

5                                                                              6 algorithm for predicting a lesion in a coronary artery based on a fractional flow reserve (FFR) according to an embodiment of the present disclosure.

Figure 3:
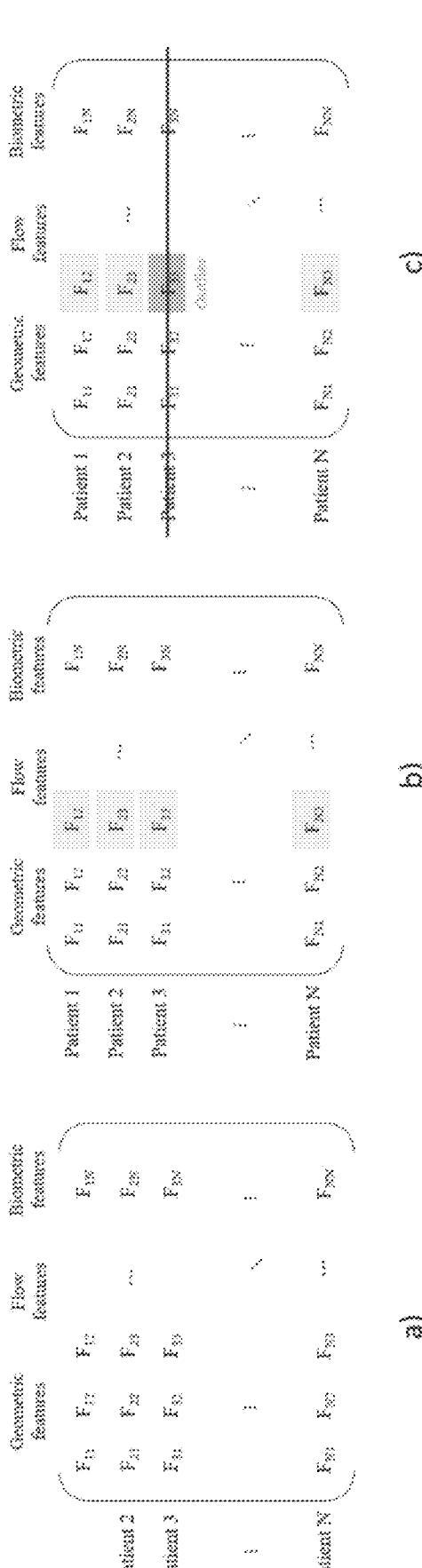

FIG. 3 provides diagrams a), b) and c) illustrating an operation of a data processing unit by an optimization system and method of an AI algorithm for predicting a lesion in a coronary artery based on an FFR according to an embodiment of the present disclosure.

Figure 4:
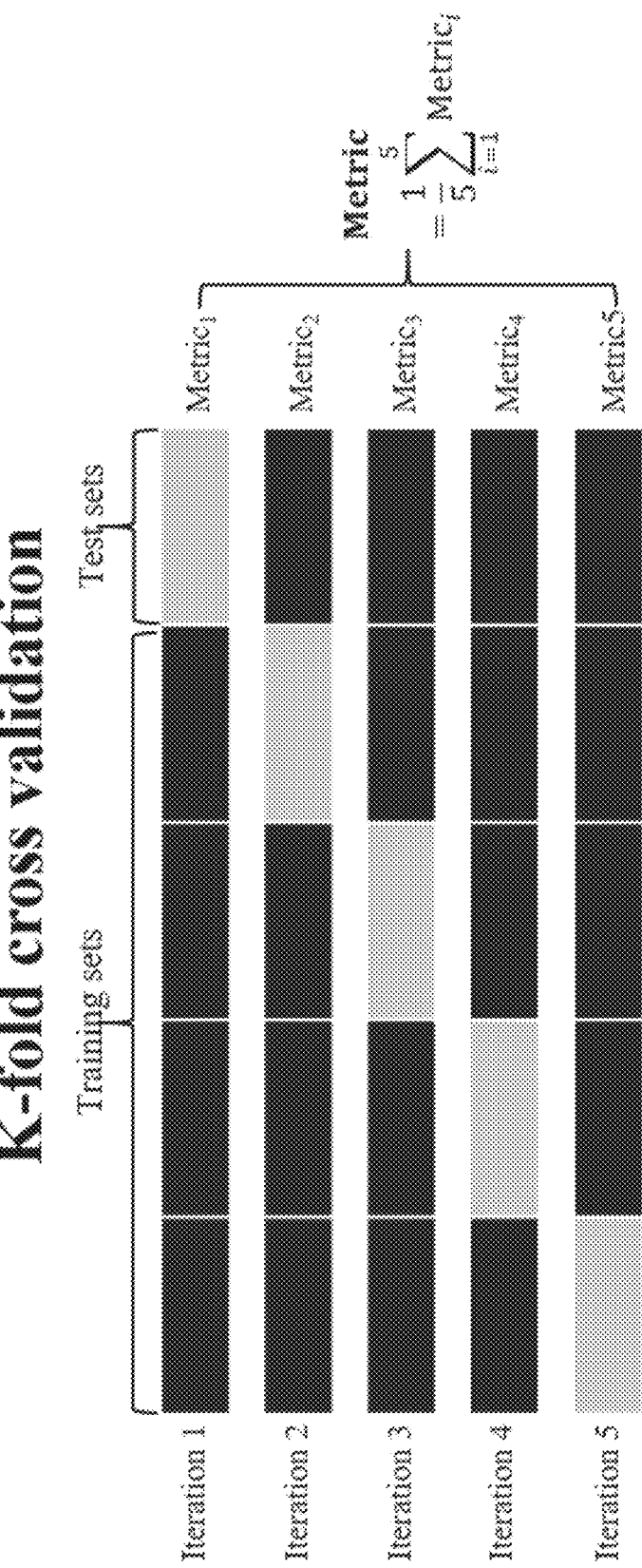

FIG. 4 is a diagram illustrating a K-fold test used for the optimization system and method of an AI algorithm for predicting a lesion in a coronary artery based on an FFR according to an embodiment of the present disclosure.

FIGS. 5 to 8 are diagrams illustrating an operation of an AI optimization analysis unit by the optimization system and method of an AI algorithm for predicting a lesion in a coronary artery based on an FFR according to an embodiment of the present disclosure.

Figure 9:
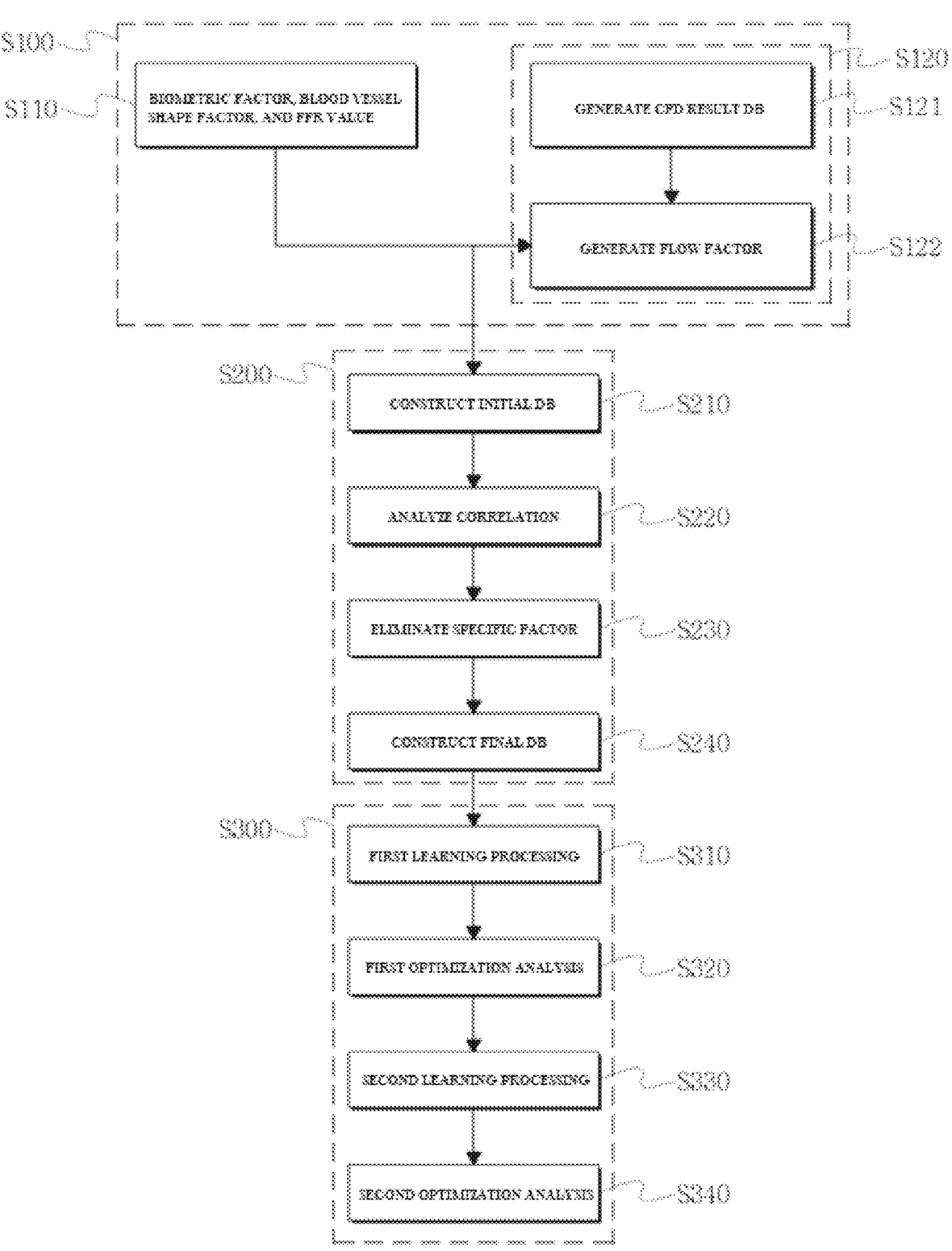

FIG. 9 is a flowchart illustrating of an optimization method of an AI algorithm for predicting a lesion in a coronary artery based on an FFR according to an embodiment of the present disclosure.

DETAILED DESCRIPTION OF MAIN ELEMENTS

100: data collection unit
110: biometric collection unit
120: shape collection unit
130: flow generation unit
131: flow DB unit
132: flow extraction unit
200: data processing unit
210: DB construction unit
220: correlation analysis unit
230: factor elimination unit
240: DB reconfiguration unit
300: AI optimization analysis unit
310: first learning processing unit
320: first optimization analysis unit
330: second learning processing unit
340: second optimization analysis unit

DETAILED DESCRIPTION OF EMBODIMENTS

Hereinafter, an optimization system and method of an artificial intelligence (AI) algorithm for predicting a lesion in a coronary artery based on a fractional flow reserve (FFR) according to the present disclosure will be described in detail with reference to the accompanying drawings. Drawings to be provided below are provided by way of example so that the spirit of the present disclosure may be sufficiently transferred to those skilled in the art. Therefore, the present disclosure is not limited to drawings to be provided below, but may be implemented in other forms. In addition, like reference numerals denote like components throughout the specification.

Technical terms and scientific terms used herein have the general meaning understood by those skilled in the art to which the present disclosure pertains unless otherwise defined, and a description for a known function and configuration unnecessarily obscuring the gist of the present disclosure will be omitted in the following description and the accompanying drawings.

In addition, a system refers to a set of components including devices, mechanisms, means, and the like, systematized in order to perform required functions and regularly interacting with each other.

When there is a lesion in a blood vessel, a perfusion pressure decreases, such that a difference in pressure between the distal part and the proximal part of the lesion site is generated, and the FFR is a value obtained by evaluating the difference in pressure. In order to evaluate the difference in pressure between the distal part and the proximal part of the lesion site, in an invasive method, a catheter that may measure a pressure inside the coronary artery is inserted into the blood vessel to measure pressures before and after a stenosis region (lesion region), and it is decided that there is no ischemic symptom when the FFR exceeds 0.8 and it is decided that there is ischemia symptom when the FFR is 0.8 or less. However, in the method using such an FFR, an invasive catheter is inserted into the blood vessel.

To address the foregoing, a method of calculating the FFR using a non-invasive coronary artery computed tomography (CT) medical image can be provided.

In detail, such a method is a technology for calculating a flow of blood by regionalizing the heart from non-invasively photographed heart region medical image data and generating a mesh capable of fluid dynamics calculation. Even in this case, a lot of time and labor are required for precise regionalization, and high computing performance for numerically analyzing fluid dynamics is required.

In addition, the FFR itself is an analysis result value of a flow in the blood vessel, but it is pointed out that predicting the flow with only a shape of the blood vessel (a shape of the regionalized heart) without analyzing the flow is low in reliability and accuracy.

In determining whether or not to perform a medical procedure using such an FFR, in a case where an FFR corresponding to a so-called 'gray zone' known as a region of uncertainty, is between 0.75 and 0.8, when the FFR is only numerically analyzed, it is general for a medical team to directly perform cardiovascular surgery, but it is not easy to make a diagnosis for surgery according to various characteristics of patients, and ultimately, a decision is made through an external factor such as an experience of the medical team.

That is, a non-invasive method can be provided in order to address invasiveness, but in spite of the non-invasive method, the decision cannot but be made through the external factor for the FFR between 0.75 and 0.8. Therefore, it is proposed to perform optimization of an artificial intelligence (AI) algorithm that calculates the FFR so that the intervention of the external factor such as the experience of the medical team in a process of determining disease treatment may be minimized by further improving reliability/accuracy of calculation of the FFR by the non-invasive method and in particular, further improving reliability/accuracy of calculation of the FFR corresponding to the gray zone.

Thus, embodiments provide a method of calculating an FFR by non-invasively regionalizing the heart from heart region medical image data through an AI algorithm or neural machine learning model and generating a mesh capable of fluid dynamics calculation to calculatingly predict a flow of blood has been utilized.

However, in a case of a non-invasive method using such an AI algorithm, the FFR itself is an analysis result value of a flow in a blood vessel, but it is pointed out that predicting the flow with only a shape of the blood vessel (a shape of the regionalized heart) without analyzing the flow is low in reliability and accuracy.

Therefore, since reliability and accuracy of the FFR calculated through the non-invasive method, in particular, an FFR corresponding to a gray zone known as a region of uncertainty are lower, a medical team has a difficulty in determining whether or not to perform a medical procedure in consideration of this.

Accordingly, the optimization system and method of an AI algorithm for predicting a lesion in a coronary artery based on an FFR according to embodiments of the present disclosure provide a technology capable of minimizing intervention of an external factor such as an experience of the medical team in a process of determining disease treatment by performing various optimization of AI algorithms utilized in order to calculate the FFR to further improve reliability/accuracy of calculation of the FFR by the non-invasive method, in particular, reliability/accuracy of calculation of the FFR corresponding to the gray zone.

That is, in order to minimize the intervention of the external factor such as the experience of the medical team in the process of determining disease treatment and utilize the FFR calculated by the non-invasive method as much as possible, it is essential to have high reliability for the gray zone.

In consideration of this, embodiments provide the optimization system and method of an AI algorithm for predicting a lesion in a coronary artery based on an FFR by performing optimization with a focus on result performance in the gray zone.

Figure 1:
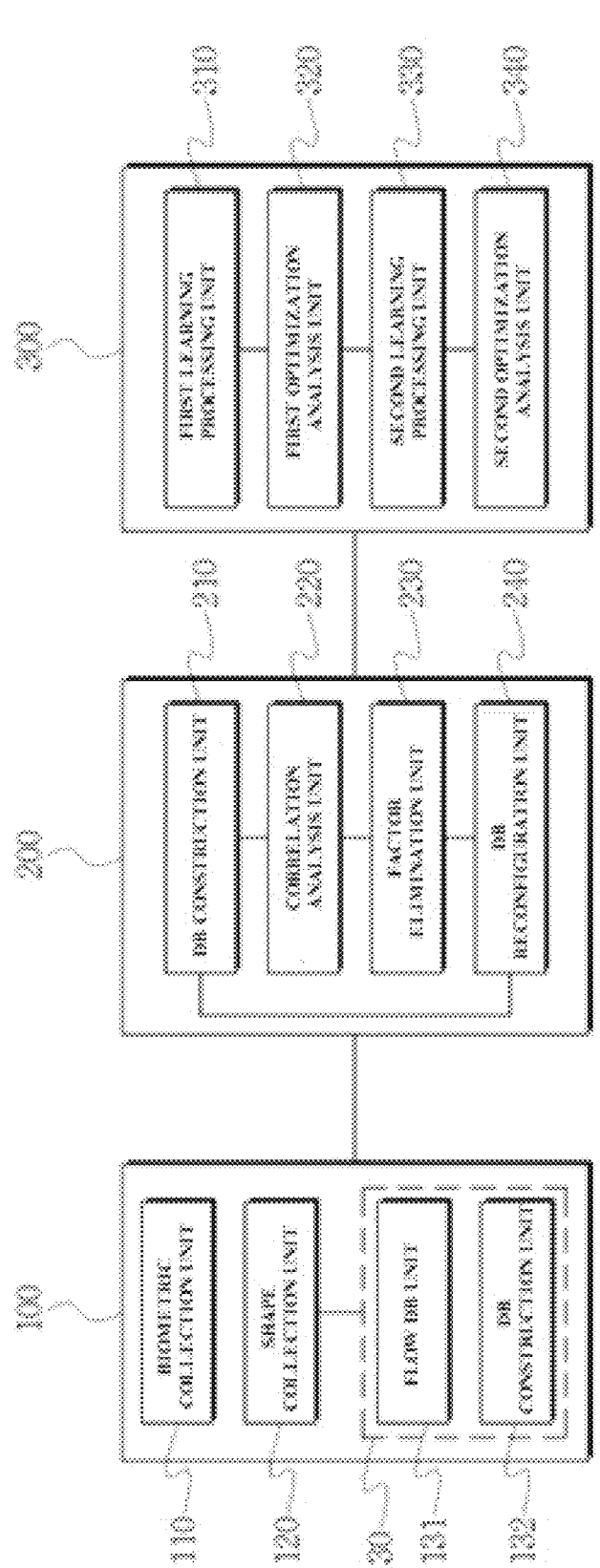
FIGS. 1 and 2 are diagrams illustrating a configuration of an optimization system of an artificial intelligence (AI)

FIG. 1 is a block diagram illustrating a configuration of an optimization system of an AI algorithm for predicting a lesion in a coronary artery based on an FFR according to an embodiment of the present disclosure. The optimization system of an AI algorithm for predicting a lesion in a coronary artery based on an FFR according to an embodiment of the present disclosure will be described in detail with reference to FIG. 1.

In embodiments, the optimization system of an AI algorithm for predicting a lesion in a coronary artery based on an FFR according to an embodiment of the present disclosure is configured to include a data collection unit 100, a data processing unit 200, and an AI optimization analysis unit 300, as illustrated in FIG. 1, and, in embodiments, the respective components are included in one arithmetic processing means or a plurality of arithmetic processing means including a computer.

Before each component is described in detail, an FFR will be described.

As described above, when there is a lesion in a blood vessel, a perfusion pressure decreases, such that a difference in pressure between the distal part $$(Q_S^{max})$$

and the proximal part $$(Q_N^{max})$$

of the lesion site is generated, and the FFR is a value obtained by evaluating the difference in pressure and is defined as represented by the following Equation 1.
[Equation 1]

$$FFR = \frac{Q_S^{max}}{Q_N^{max}} \text{ (empiric definition)}$$

Here, Q is a ratio of the difference in pressure (P) of the coronary artery to resistance (R), and may thus be replaced as represented by the following Equation 2.
[Equation 2]

$$FFR = \frac{(P_d - P_V)/R_S^{max}}{(P_a - P_V)/R_N^{max}}$$

(Here, Pd refers to a pressure distal to the lesion, Pa refers to a pressure proximal to the lesion, and Pv refers to a mean central venous pressure.)

Since measurement is performed in a maximum blood flow state, the resistance is equally minimal and is thus canceled, and Pv is negligible as compared with $P_a$ or $P_d$, the FFC may finally be defined as represented by the following Equation 3.
[Equation 3]

$$FFR = \frac{P_d}{P_a}$$

The respective components will be described in detail based on this.

In embodiments, the data collection unit 100 collects preset factor data in order to predict an FFR numerical value.

Here, the preset factor data generally refer to collected data required for learning in an AI learning model that calculates an FFR.

Therefore, in order to apply the factor data to various AI algorithms, in embodiments, the data collection unit 100 collects factor data of as many patients as possible, but when an AI algorithm is fixed to a specific AI algorithm and collected data required for learning in the corresponding artificial intelligence algorithm are fixed, the data collection unit 100 may also collect the fixed collected data.

In embodiments, the data collection unit 100 is configured to include a biometric collection unit 110, a shape collection unit 120, and a flow generation unit 130 including a flow database (DB) unit 313 and a flow extraction unit 132, as illustrated in FIG. 1. In embodiments, the data collection unit 100 receives FFR values measured or predicted for each patient.

Since the optimization system of an AI algorithm for predicting a lesion in a coronary artery based on an FFR according to an embodiment of the present disclosure is a technology of optimizing an AI algorithm so that learning is performed with high accuracy and reliability of results, rather than calculating and providing the FFR using an AI model that has already been trained, the data collection unit 100 receives the FFR values measured or predicted for each patient, which is correct answer data in order to evaluate the accuracy and the reliability of the results.

Figure 2:
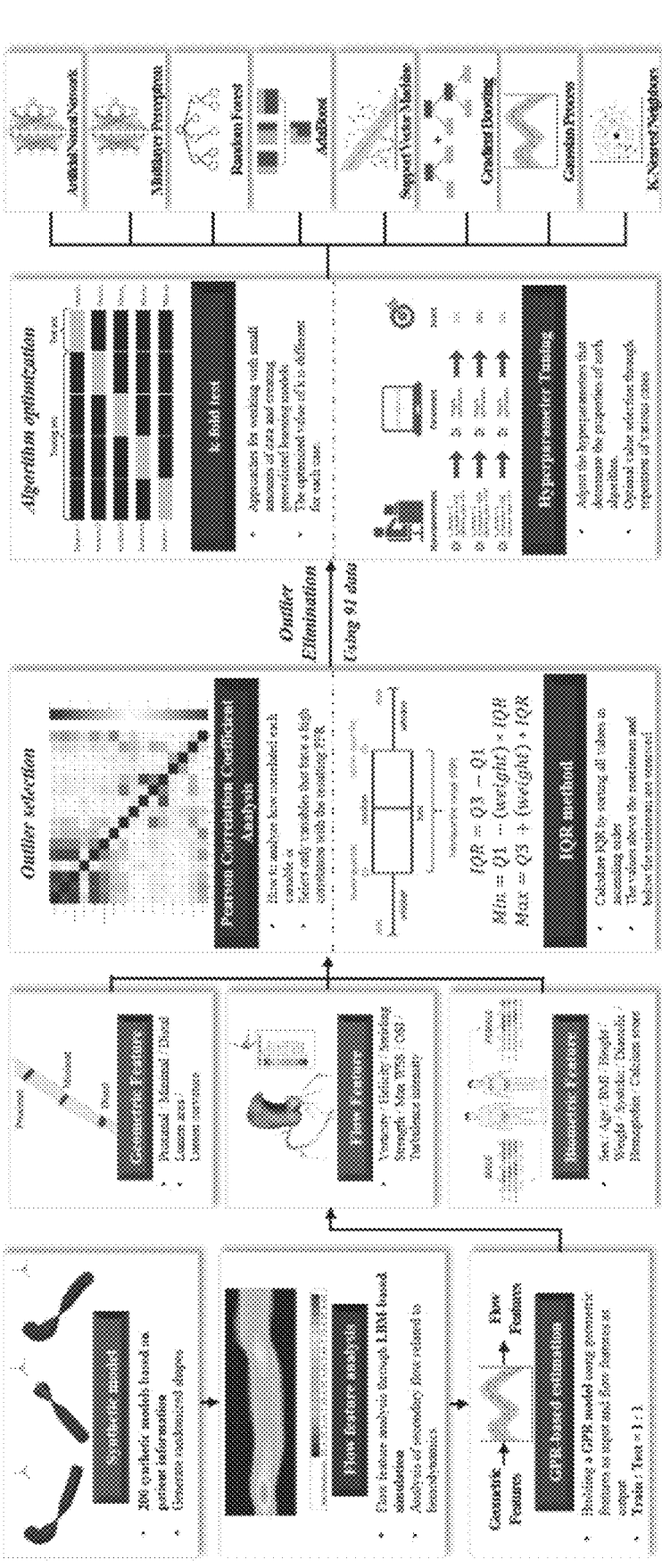

In embodiments, the biometric collection unit 110 corresponds to 'Biometric Feature' illustrated in FIG. 2, and receives biometric factor data for each patient from the outside. The biometric factor data is configured to include a gender, an age, a body mass index (BMI), a height, a weight, a blood pressure, a hemoglobin level, calcium, and the like, for each patient.

In embodiments, the shape collection unit 120 receives blood vessel shape factor data generated based on medical image data for each patient from the outside, and corresponds to 'Geometric Feature' illustrated in FIG. 2.

The vessel shape factor data is configured to include a proximal part, a distal part, a minimal part, a lumen area, a lumen curvature, and the like, of the lesion site of the patient.

The flow generation unit 130 generates flow factor data for a cardiovascular region for each patient using the blood vessel shape factor data received by the shape collection unit 120. The flow generation unit 130 corresponds to the 'Flow Feature' illustrated in FIG. 2, and the flow factor data is configured to include Vorticity, Helicity, Swirling Strength, Max WSS, OSI, Turbulence Intensity, and the like.

The flow generation unit 130 substitutes the blood vessel shape factor data by the shape collection unit 120 through a shape factor-flow factor database through a computational fluid dynamics simulation based on a virtual blood vessel model generated in advance to extract the corresponding flow factor data.

In embodiments, the flow DB unit 131 generates a plurality of virtual blood vessel models in advance and performs a computational fluid dynamics (CFD) simulation for the generated virtual blood vessel models by applying a pre-stored technique. A database of the flow factor data according to a simulation result is constructed to store and manage the flow factor data. In this embodiment, blood vessel shape factor data for a corresponding virtual blood vessel model from which a result of the flow factor data is derived are matched and a database is constructed.

In embodiments, the flow DB unit 131 performs a computational fluid dynamics simulation based on a lattice Boltzmann method (LBM), but this is only an example of the present disclosure.

In more detail, the LBM refers to a method of approximating a fluid to an aggregate (lattice fluid model) of virtual particles to sequentially develop collision and translation of each particle using a velocity distribution function of a particle and calculating a moment of the particle to calculate a flow field of the fluid. Therefore, in a case of performing a simulation based on the LBM, velocity and pressure values for each lattice in a simulation domain may be obtained as a result through which a flow factor value may be calculated. Based on such a point, a flow factor derived by calculation by the flow generation unit 130 is configured to include Vorticity, Helicity, Swirling Strength, Max WSS, OSI, and Turbulence Intensity.

In embodiments, the flow extraction unit 132 derives performing result data corresponding to the blood vessel shape factor data by the shape collection unit 120 based on the data stored and managed by the flow DB unit 131 and generates the performing result data as the flow factor data.

As discussed above, when a numerical analysis is performed on fluid dynamics every time a learning model through an AI algorithm is generated, high computing resources may be required.

In address the foregoing, a process requiring high computing resources in advance is processed through the flow DB unit 131, and a database of processing result data is then constructed to store and manage the processing result data.

Through this, the flow extraction unit 132 can derive the performing result data corresponding to the blood vessel shape factor data by the shape collection unit 120 based on the data stored and managed by the flow DB unit 131 and extracts the performing result data as the flow factor data.

The data processing unit 200 analyzes a correlation between the factor data collected by the data collection unit 100 and performs elimination of specific factor data, that is, outlier elimination.

To this end, in embodiments, the data processing unit 200 is configured to include a DB construction unit 210, a correlation analysis unit 220, a factor elimination unit 230, and a DB reconfiguration unit 240, as illustrated in FIG. 1.

In embodiments, the DB construction unit 210 constructs a database of the biometric factor data, the blood vessel shape factor data, and the flow factor data by the data collection unit 100 for each patient to store and manage the biometric factor data, the blood vessel shape factor data, and the flow factor data, as illustrated in a) of FIG. 3.

In embodiments, the correlation analysis unit 220 analyzes a correlation between each detailed factor data constituting all factor data by the DB construction unit 210 and the received FFR by applying a pre-stored technique.

That is, the correlation analysis unit 220 analyzes a correction between the respective detailed factor data (a gender, an age, a BMI, a height, a weight, a blood pressure, a hemoglobin level, calcium, a proximal part, a distal part, a minimal part, a lumen area, a lumen curvature, and the like, of the lesion site, Vorticity, Helicity, Swirling Strength, Max WSS, OSI, and Turbulence Intensity for each patient) constituting all factor data (biometric factor data, blood vessel shape factor data, and flow factor data for each patient) by the DB construction unit 210 and the FFR, which is correct answer data, received by the data collection unit 100.

To this end, in embodiments, a person correlation coefficient analysis technique is applied. In detail, in a case of a person correlation coefficient heatmap, since it may be seen that a correlation between factors becomes greater as a color becomes darker, detailed factor data having the greatest correlation with the FFR for each patient are selected, as illustrated in b) of FIG. 3, based on this.

In embodiments, the factor elimination unit 230 eliminates all factor data of the corresponding patient including detailed factor data having the greatest correlation with the FFR when the detailed factor data having the greatest correlation with the FFR is a predetermined reference or less based on an analysis result by the correlation analysis unit 220 by applying a pre-stored technique.

That is, the factor elimination unit 230 uses a first quartile (lower quartile) and a third quartile (upper quartile), a median value between the first quartile and the third quartile, and weight values each applied to the first quartile and the third quartile by applying an interquartile range (IQR) technique.

In detail, in a case of applying the IQR technique, when a correlation value corresponding to the detailed factor data having the greatest correlation with the FFR for each patient is smaller than a minimum value or greater than a maximum value, the factor elimination unit 230 selects the detailed factor data as elimination target factor data.

Through this, the factor elimination unit 230 eliminates all factor data of the patient including the elimination target factor data, as illustrated in c) of FIG. 3.

This becomes a factor hindering learning performance in a case of data having high uncertainty among a small number of data because the number of collectable data is absolutely insufficient in a case of clinical data. Therefore, eliminating all factor data of the patient including the elimination target factor data results in improving learning performance.

Through this process, in embodiments, the DB reconstruction unit 240 corrects and reconstructs the database by the DB construction unit 210 based on an elimination result by the factor elimination unit 230.

In embodiments, the AI optimization analysis unit 300 performs learning processing using the factor data from which the specific factor data have been eliminated by the data processing unit 200, in other words, the database reconstructed by the DB reconstruction unit 240, by using a plurality of pre-stored AI algorithms. In addition, optimization processing of each AI algorithm is performed based on an analysis result.

To this end, in embodiments, the AI optimization analysis unit 300 is configured to include a first learning processing unit 310, a first optimization analysis unit 320, a second learning processing unit 330, and a second optimization analysis unit 340, as illustrated in FIG. 1.

In this case, the first learning processing unit 310 and the second learning processing unit 320 perform learning processing for a plurality of pre-stored heterogeneous AI algorithms. In this embodiment, the plurality of pre-stored heterogeneous AI algorithms are configured to include an Artificial Neural Network, Multi-layer Perceptron, Random Forest, AdaBoost, Support Vector Machine, Gradient Boosting, Gaussian Process, and K-Nearest Neighbors, as illustrated in FIG. 2.

However, these are algorithms arbitrarily selected by the present applicant as examples in order to test prediction accuracy of the FFR, and in addition to these algorithms, an AI algorithm may be applied, and even though an AI algorithm that is not mentioned above is applied, optimization processing may be performed by performing an operation of the AI optimization analysis unit 300 to be described later.

The first learning processing unit 310 performs learning processing by inputting the database by the DB reconstruction unit 240 as training data to a plurality of pre-stored AI algorithms.

In this case, the first learning processing unit 310 divides all data included in the database by the DB reconstruction unit 240 into training data and test data according to a plurality of predetermined ratios by applying a pre-stored technique, and then inputs each training data to each AI algorithm to perform learning processing.

In detail, the first learning processing unit 310 divide all data (all data included in the database by the DB reconstruction unit 240) into training data (training sets) and test data (test sets) and divides all data in any k fold ratios (a plurality of predetermined ratios), by applying a K-fold cross validation technique illustrated in FIG. 4.

Through this, k−1 of all data are used as training data and the other one of all data is used as test data, and since all data are divided into k data, a total of k different verification data are generated. That is, cross-performance measurement may be performed k times.

As such, the reason for applying the K-fold cross validation technique is that elimination of the factors are additionally performed from the insufficient clinical data as described above, and thus, the training data becomes more insufficient. To address the foregoing, in embodiments, by applying the K-fold cross validation technique, k different validation data (training data+test data) are generated, each learning processing is performed, and performance results for learning results are integrated with each other to derive a single result, thereby performing a generalized learning model performance evaluation.

In other words, the first learning processing unit 310 performs learning processing by inputting training data generated by applying the K-fold cross validation technique to each AI algorithm.

The learning processing is performed k times in total for each AI algorithm, and as a result, a total of k learning result models are generated for each AI algorithm.

In consideration of this point, the first optimization analysis unit 320 uses a single prediction performance result obtained by integrating prediction performance results by the total of k learning result models generated for each AI algorithm in analyzing a prediction performance result.

As an example, when the learning processing is performed five times on an AI algorithm A, five learning result models M_A1, M_A2, M_A3, M_A4, and M_A5 are output as a result of the learning processing by the first learning processing unit 310.

The first optimization analysis unit 320 does not analyze each prediction result by the five learning result models, but analyzes a single prediction result (average value, etc.) obtained by integrating prediction results by the five learning result models through the AI algorithm A, in using the learning result model for each AI algorithm by the first learning processing unit 310.

In consideration of this point, the first optimization analysis unit 320 receives FFR prediction results output from the learning result model for each AI algorithm by the first learning processing unit 310. In this case, the FFR force prediction results may be a total of k prediction results. Here, in order to receive the FFR prediction results output from the learning result model for each AI algorithm, in embodiments, the test data are inputted by the first learning processing unit 310.

In embodiments, the first optimization analysis unit 320 analyzes accuracy of the single prediction performance result obtained by integrating the prediction results (FFR prediction results) output for each learning result model for each AI algorithm. In this embodiment, the analysis of the accuracy is performed using the FFR, which is the correct answer data input for each patient by the data collection unit 100.

Accuracy and reliability of the learning result model are evaluated as a mean absolute error (MAE) and an $R^2$ score, which are defined by the following Equations 4 and 5, respectively.

[Equation 4]

$$MAE = \frac{\sum_{i=1}^{n} |y_i - x_i|}{n}$$

$y_i$ = prediction $x_i$ = true value $n$ = total number of data points

[Equation 5]

$$R^2 = 1 - \frac{RSS}{TSS}$$

$RSS$ = sum of squares of residuals $TSS$ = total sum of squares

Through this, the accuracy analyzed for the single prediction performance result obtained by integrating the prediction results output by each learning result model for each AI algorithm, which is an analysis result through the first optimization analysis unit 320 may be represented as illustrated in FIG. 5.

In this case, a learning process is performed k times in total in consideration of the predetermined ratio k set by the first learning processing unit 310 for each AI algorithm, and it may be seen that accuracy is different according to k as illustrated in FIG. 5. It may be seen that the greatest difference (0.0128) in the MAE according to the k value is a Gaussian Process algorithm and the greatest difference (0.1636) in the $R^2$ score is an AdaBoost algorithm.

In embodiments, the first optimization analysis unit 320 analyzes accuracy of the FFR prediction result (integrated single prediction performance result) output from the k learning result models for each AI algorithm, through such an analysis process to derive the most optimized k for each AI algorithm, in other words, a specific ratio (the most optimized k) having the highest FFR prediction result for each AI algorithm.

FIG. 6 is a table illustrating accuracy analysis results by a learning result model generated by applying a database before being corrected and a database after being corrected by the data processing unit 200 to each AI algorithm. A k-fold was limited to 5-fold, which is the most basic recommended method when using the K-fold cross validation technique, through an experiment, and it may be seen as an analysis result that the MAE entirely decreases while the $R^2$ score increases. It may be seen that in the Artificial Neural Network, prediction result accuracy (MAE decreases from 0.0747 to 0.0414 and $R^2$ score increases from 0.183 to 0.521) has been most improved through an outlier elimination process by the data processing unit 200.

Through such an experiment, an improvement effect of the prediction result accuracy by the outlier elimination process by the data processing unit 200 may be confirmed.

FIGS. 7A to 7D are graphs illustrating FFR prediction accuracy corresponding to a gray zone (FFR of 0.75 to 0.8) and an extended gray zone (FFR of 0.7 to 0.85) by the learning result model generated for each AI algorithm. In order to confirm an effect due to deriving a specific ratio (the most optimized k) having the highest FFR prediction result using the K-fold cross validation technique, k has been limited to being selected as 3 to 7 to generate each learning result model.

Figure 7:
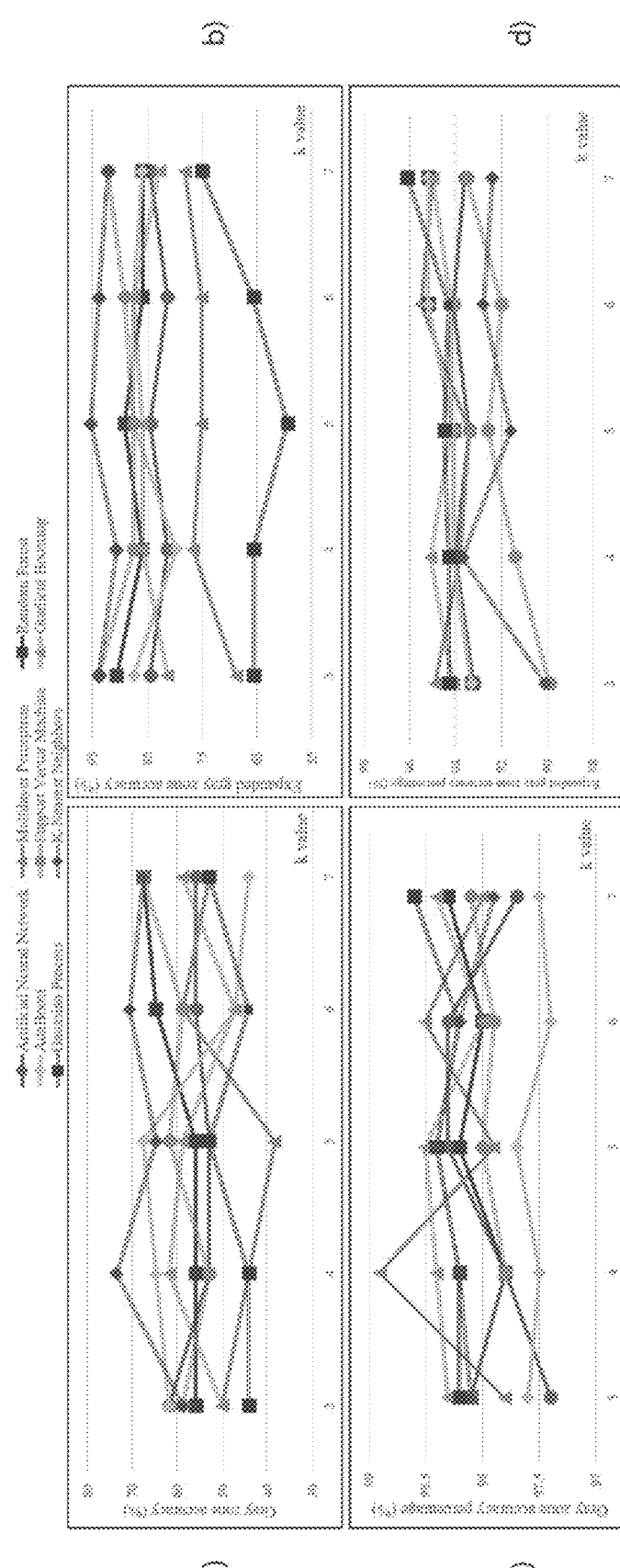

In detail, a) of FIG. 7 illustrates accuracy in the gray zone, b) of FIG. 7 illustrates accuracy in the extended gray zone, c) of FIG. 7 illustrates an accuracy percentage in the gray zone, and d) of FIG. 7 illustrates an accuracy percentage in the extended gray zone. Through such an experiment, as described above, it may be seen that the accuracy according to the k value is different, and the improvement effect of the prediction result accuracy by the most optimized k may be confirmed.

In this embodiment, the optimization system of an AI algorithm for predicting a lesion in a coronary artery based on an FFR according to an embodiment of the present disclosure performs weight control on a hyper parameter that determines an attribute for each AI algorithm in order to further improve the accuracy and the reliability of the prediction result.

In detail, in embodiments, the second learning processing unit 330 controls a weight for a hyper parameter that determines a property for each of a plurality of pre-stored AI algorithms by applying a pre-stored technique, and inputs the training data divided according to the specific ratio (the most optimized k) having the highest FFR prediction result derived by the first optimization analysis unit 320 to each controlled AI algorithm to perform learning processing.

In this case, the pre-stored technique is configured to include a hyper-parameter tuning technique, as illustrated in FIG. 2, and an optimal value is selected through iterative learning processing in various control cases.

In embodiments, the hyper parameters refer to parameters that may need to be set before the learning process is performed. Hyper parameter tuning refers to an operation of tuning values of hyper parameters in order to maximize performance of the learning result model. Since the performance of the learning result model significantly varies depending on values to which the hyper parameters are set, optimization of the values of the hyper parameters is one of the most important operations.

The second optimization analysis unit 340 receives an FFR prediction result for each learning result model by the second learning processing unit 330 using the test data divided according to the specific ratio (the most optimized k) having the highest FFR prediction result derived by the first optimization analysis unit 320 and the received FFR. In this case, since k most optimized learning result models are generated for each AI algorithm, in embodiments, the second optimization analysis unit 340 analyzes accuracy of an FFR prediction result (integrated single prediction performance result) output from the k most optimized learning result models, like the first optimization analysis unit 320.

In this case, the second learning processing unit 330 repeatedly performs learning processing for each controlled AI algorithm as it controls weights for the corresponding hyper parameters for each AI algorithm plural times under different conditions.

Therefore, in embodiments, the second optimization analysis unit 340 analyzes accuracy of an FFR prediction result (integrated single prediction performance result) for k most optimized learning result model sets for each of the AI algorithms generated as many as the number of times of the weight control to derive a weight control condition of a hyper parameter corresponding to a learning result model having the highest FFR prediction accuracy for each AI algorithm.

In embodiments, the learning processing is performed by applying the specific ratio (the most optimized k) having the highest FFR prediction result derived by the first optimization analysis unit 320 and a weight control condition of the hyper parameter having the highest FFR prediction result derived by the second optimization analysis unit 340 for each AI algorithm based on such an analysis result of the AI optimization analysis unit 300.

FFR prediction results by the learning result model according to the learning processing result considering such an optimization condition (the specific ratio (the most optimized k) having the highest FFR prediction result and the weight control condition of the hyper parameter having the highest FFR prediction result) are illustrated in FIGS. 8 and 9.

FIG. 8 illustrates accuracy in the gray zone, an accuracy percentage in the gray zone, accuracy in the extended gray zone, and an accuracy percentage in the extended gray zone by a learning result model learning-processed by applying training data processing according to most optimized k for each AI algorithm and the weight control condition of the hyper parameter.

Through an analysis by an experiment, it may be seen that Multi-layer Perceptron has the highest gray zone accuracy percentage (98.9%), and it may be seen that Gaussian Process has the highest extended gray zone accuracy percentage (96.1%). Furthermore, since it may be seen that accuracy in the gray zone is higher than 97% for all AI algorithms, reliability is naturally increased.

FIG. 9 is a flowchart illustrating of an optimization method of an AI algorithm for predicting a lesion in a coronary artery based on an FFR according to an embodiment of the present disclosure. The optimization method of an AI algorithm for predicting a lesion in a coronary artery based on an FFR according to an embodiment of the present disclosure will be described in detail with reference to FIG. 9.

The optimization method of an AI algorithm for predicting a lesion in a coronary artery based on an FFR according to an embodiment of the present disclosure is a method that uses the optimization system of an AI algorithm for predicting a lesion in a coronary artery based on an FFR according to an embodiment of the present disclosure in which each step is performed by an arithmetic processing means including a computer, and includes a data collection step (S100), a data processing step (S200), and an optimization analysis step (S300).

The respective steps will be described in detail.

In the data collection step (S100), the data collection unit 100 collects preset factor data in order to predict an FFR numerical value.

Here, the preset factor data generally refer to collected data required for learning in an AI learning model that calculates an FFR.

Therefore, in order to apply the factor data to various AI algorithms, in embodiments, the data collection unit 100 collects factor data of as many patients as possible, but when an AI algorithm is fixed to a specific AI algorithm and collected data required for learning in the corresponding artificial intelligence algorithm are fixed, the data collection unit 100 may also collect the fixed collected data.

The data collection step (S100) is configured to include an input step (S110) and a generation step (S120), as illustrated in FIG. 9.

In the input step (S110), biometric factor data for each patient (a gender, an age, a BMI, a height, a weight, a blood pressure, a hemoglobin level, calcium, and the like, for each patient) corresponding to 'Biometric Feature' illustrated in FIG. 2 and blood vessel shape factor data corresponding to 'Geometric Feature' illustrated in FIG. 2 and generated based on medical image data for each patient (a proximal part, a distal part, a minimal part, a lumen area, a lumen curvature, and the like, of the lesion site of the patient) are input, together with an FFR value measured or predicted for each patient.

In the generation step (S120), flow factor data for a cardiovascular region for each patient (corresponding to the 'Flow Feature' illustrated in FIG. 2 and including Vorticity, Helicity, Swirling Strength, Max WSS, OSI, Turbulence Intensity, and the like) are generated using the blood vessel shape factor data by the input step (S110), and a DB generation step (S121) and a flow extraction step (S122) are performed.

In the generation step (S120), the blood vessel shape factor data are substituted through a shape factor-flow factor database through a computational fluid dynamics simulation based on a virtual blood vessel model generated in advance to extract the corresponding flow factor data.

In the DB generation step (S121), in embodiments, a plurality of virtual blood vessel models are generated in advance and a computational fluid dynamics (CFD) simulation for the generated virtual blood vessel models by applying a pre-stored technique is performed. A database of the flow factor data according to a simulation result is constructed to store and manage the flow factor data. In this case, blood vessel shape factor data for a corresponding virtual blood vessel model from which a result of the flow factor data is derived are matched and a database is constructed.

Here, in embodiments, the flow DB unit 131 performs a computational fluid dynamics simulation based on a lattice Boltzmann method (LBM), but this is only an example of the present disclosure.

In the flow extraction step (S122), performing result data corresponding to the blood vessel shape factor data by the input step (S110) are derived based on the data by the DB generation step (S121), and are generated as the flow factor data.

In the data processing step (S200), the data processing unit 200 analyzes a correlation between the factor data by the data collection step (S100) and performs elimination of specific factor data, that is, outlier elimination.

To this end, in the data processing step (S200), as illustrated in FIG. 9, an initial DB construction step (S210), a correlation analysis step (S220), a factor elimination step (S230), and a final DB construction step (S240) are performed.

In the DB construction step (S210), a database of the biometric factor data, the blood vessel shape factor data, and the flow factor data by the data collection step (S100) for each patient is constructed to store and manage the biometric factor data, the blood vessel shape factor data, and the flow factor data, as illustrated in a) of FIG. 3.

In the correlation analysis step (S220), a correlation between each detailed factor data constituting all factor data by the initial DB construction step (S210) and the received FFR is analyzed by applying a pre-stored technique.

In detail, in the correlation analysis step (S220), a correction between the respective detailed factor data (a gender, an age, a BMI, a height, a weight, a blood pressure, a hemoglobin level, calcium, a proximal part, a distal part, a minimal part, a lumen area, a lumen curvature, and the like, of the lesion site, Vorticity, Helicity, Swirling Strength, Max WSS, OSI, and Turbulence Intensity for each patient) constituting all factor data (biometric factor data, blood vessel shape factor data, and flow factor data for each patient) by the initial DB construction step (S210) and the FFR, which is correct answer data, received by the data collection step (S100), is analyzed.

To this end, in embodiments, a person correlation coefficient analysis technique is applied. In detail, in a case of a person correlation coefficient heatmap, since it may be seen that a correlation between factors becomes greater as a color becomes darker, detailed factor data having the greatest correlation with the FFR for each patient are selected, as illustrated in b)_of FIG. 3, based on this.

In the factor elimination step (S230), all factor data of the corresponding patient including detailed factor data having the greatest correlation with the FFR are eliminated when the detailed factor data having the greatest correlation with the FFR is a predetermined reference or less based on an analysis result of the correlation analysis step (S220) by applying a pre-stored technique.

That is, in the factor elimination step (S230), a first quartile (lower quartile) and a third quartile (upper quartile), a median value between the first quartile and the third quartile, and weight values each applied to the first quartile and the third quartile are used by applying an interquartile range (IQR) technique.

In detail, in the factor elimination step (S230), in a case of applying the IQR technique, when a correlation value corresponding to the detailed factor data having the greatest correlation with the FFR for each patient is smaller than a minimum value or greater than a maximum value, the detailed factor data are selected as elimination target factor data.

Through this, all factor data of the patient including the elimination target factor data are eliminated, as illustrated in c) of FIG. 3.

This becomes a factor hindering learning performance in a case of data having high uncertainty among a small number of data because the number of collectable data is absolutely insufficient in a case of clinical data. Therefore, eliminating all factor data of the patient including the elimination target factor data results in improving learning performance.

In the final DB construction step (S240), the database by the initial DB construction step (S210) is corrected and reconstructed based on an elimination result by the factor elimination step (S230).

In the optimization analysis step (S300), the AI optimization analysis unit 300 performs learning processing using the factor data from which the specific factor data have been eliminated by the final DB construction step (S240), by using a plurality of pre-stored AI algorithms. In addition, optimization processing of each AI algorithm is performed based on an analysis result.

In the optimization analysis step (S300), as illustrated in FIG. 9, a first learning processing step (S310), a first optimization analysis step (S320), a second learning processing step (S330), and a second optimization analysis step (S340) are performed.

In the first learning processing step (S310) and the second learning processing step (S330), learning processing is performed for a plurality of pre-stored heterogeneous AI algorithms. In this embodiment, the plurality of pre-stored heterogeneous AI algorithms are configured to include an Artificial Neural Network, Multi-layer Perceptron, Random Forest, AdaBoost, Support Vector Machine, Gradient Boosting, Gaussian Process, and K-Nearest Neighbors, as illustrated in FIG. 2.

However, these are algorithms arbitrarily selected by the present applicant as examples in order to test prediction accuracy of the FFR, and in addition to these algorithms, an AI algorithm may be applied, and even though an AI algorithm that is not mentioned above is applied, optimization processing may be performed by performing an operation of the AI optimization analysis unit 300 to be described later.

In the first learning processing step (S310), learning processing is performed by inputting the database by the final DB construction step (S240) as training data to a plurality of pre-stored AI algorithms.

In this case, in the first learning processing step (S310), all data included in the database by the final DB construction step (S240) are divided into training data and test data according to a plurality of predetermined ratios by applying a pre-stored technique, and each training data is then input to each AI algorithm to perform learning processing.

In detail, all data (all data included in the database by the final DB construction step (S240)) are divided into training data (training sets) and test data (test sets) and are divided in any k fold ratios (a plurality of predetermined ratios), by applying a K-fold cross validation technique illustrated in FIG. 4.

Through this, k−1 of all data are used as training data and the other one of all data is used as test data, and since all data are divided into k data, a total of k different verification data are generated. That is, cross-performance measurement may be performed k times.

As such, the reason for applying the K-fold cross validation technique is that elimination of the factors are additionally performed from the insufficient clinical data as described above, and thus, the training data becomes more insufficient. To address the foregoing, in embodiments, by applying the K-fold cross validation technique, k different validation data (training data+test data) are generated, each learning processing is performed, and performance results for learning results are integrated with each other to derive a single result, thereby performing a generalized learning model performance evaluation.

In other words, in the first learning processing step (S310), learning processing is performed by inputting training data generated by applying the K-fold cross validation technique to each AI algorithm.

The learning processing is performed k times in total for each AI algorithm, and as a result, a total of k learning result models are generated for each AI algorithm.

In consideration of this point, in the first optimization analysis step (S320), a single prediction performance result obtained by integrating prediction performance results by the total of k learning result models generated for each AI algorithm is used in analyzing a prediction performance result.

As an example, when the learning processing is performed five times on an AI algorithm A, five learning result models M_A1, M_A2, M_A3, M_A4, and M_A5 are output as a result of the learning processing by the first learning processing unit 310.

In the first optimization analysis step (S320), each prediction result by the five learning result models is not analyzed, but a single prediction result (average value, etc.) obtained by integrating prediction results by the five learning result models through the AI algorithm A is analyzed, in using the learning result model for each AI algorithm by the first learning processing step (S310).

In consideration of this point, in the first optimization analysis step (S320), FFR prediction results are output from the learning result model for each AI algorithm by the first learning processing step (S310). In this case, the FFR force prediction results may be a total of k prediction results. Here, in order to receive the FFR prediction results output from the learning result model for each AI algorithm, in embodiments, the test data are inputted by the first learning processing step (S310).

In the first optimization analysis step (S320), in embodiments, accuracy of the single prediction performance result obtained by integrating the prediction results (FFR prediction results) output for each learning result model for each AI algorithm is analyzed. In this case, the analysis of the accuracy is performed using the FFR, which is the correct answer data input for each patient by the data collection step (S100).

Accuracy and reliability of the learning result model are evaluated as a mean absolute error (MAE) and an $R^2$ score, and the accuracy analyzed for the single prediction performance result obtained by integrating the prediction results output by each learning result model for each AI algorithm, which is an analysis result through the first optimization analysis step (S320) may be represented as illustrated in FIG. 5.

In this case, a learning process is performed k times in total in consideration of the predetermined ratio k set for each AI algorithm, and it may be seen that accuracy is different according to k as illustrated in FIG. 5. It may be seen that the greatest difference (0.0128) in the MAE according to the k value is a Gaussian Process algorithm and the greatest difference (0.1636) in the $R^2$ score is an AdaBoost algorithm.

Through such an analysis process, in the first optimization analysis step (S320), accuracy of the FFR prediction result (integrated single prediction performance result) output from the k learning result models for each AI algorithm is analyzed to derive the most optimized k for each AI algorithm, in other words, a specific ratio (the most optimized k) having the highest FFR prediction result for each AI algorithm.

In the optimization method of an AI algorithm for predicting a lesion in a coronary artery based on an FFR according to an embodiment of the present disclosure, weight control is performed on a hyper parameter that determines an attribute for each AI algorithm in order to further improve the accuracy and the reliability of the prediction result.

In detail, in the second learning processing step (S330), a weight for a hyper parameter that determines a property for each of a plurality of pre-stored AI algorithms is controlled by applying a pre-stored technique, and the training data divided according to the specific ratio (the most optimized k) having the highest FFR prediction result derived by the first optimization analysis step (S320) is input to each controlled AI algorithm to perform learning processing.

In this case, the pre-stored technique is configured to include a hyper-parameter tuning technique, as illustrated in FIG. 2, and an optimal value is selected through iterative learning processing in various control cases.

In the second optimization analysis step (S340), an FFR prediction result for each learning result model by the second learning processing step (S330) is received using the test data divided according to the specific ratio (the most optimized k) having the highest FFR prediction result derived by the first optimization analysis step (S320) and the received FFR. In this case, since k most optimized learning result models are generated for each AI algorithm, in the second optimization analysis step (S340), in embodiments, accuracy of FFR an prediction result (integrated single prediction performance result) output from the k most optimized learning result models is analyzed, like the first optimization analysis step (S320).

In the second learning processing step (S330), learning processing is repeatedly performed for each controlled AI algorithm as it controls weights for the corresponding hyper parameters for each AI algorithm plural times under different conditions.

Therefore, in the second optimization analysis step (S340), accuracy of an FFR prediction result (integrated single prediction performance result) for k most optimized learning result model sets for each of the AI algorithms generated as many as the number of times of the weight control is analyzed to derive a weight control condition of a hyper parameter corresponding to a learning result model having the highest FFR prediction accuracy for each AI algorithm.

A learning model having high prediction result accuracy/reliability may be generated by applying the specific ratio (the most optimized k) having the highest FFR prediction result and a weight control condition of the hyper parameter having the highest FFR prediction result for each AI algorithm based on such an analysis result of the optimization analysis step (S300) to perform the learning processing.

The optimization system and method of an AI algorithm for predicting a lesion in a coronary artery based on an FFR according to the present disclosure having the configuration as described above may be a non-invasive method, and may decrease invasive measuring processes through the optimization of the AI algorithm capable of calculating the FFR to decrease a burden of the patient in terms of cost and the possibility of side effects.

In addition, the FFR may be calculated with very high accuracy and reliability through the learning result model by the optimized AI algorithm, and may thus help a doctor to make a clinical diagnosis of a coronary artery.

In particular, through the optimization of the AI algorithm, the prediction accuracy and reliability of the FFR corresponding to the gray zone may be significantly increased, such that various expected effects may be created as a technology used by doctors in a clinical field.

Through this, both doctors and patients may decrease unnecessary processes, and may utilize FFR values having high prediction accuracy/reliability, such that a social cost may be expected to be decreased.

Logical blocks, components, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

The present disclosure has been described by specific matters such as detailed components, embodiments, and the drawings hereinabove, but they have been provided for assisting in the entire understanding of the present disclosure, and the present disclosure is not limited to embodiments. Various modifications and changes may be made by those skilled in the art to which the present disclosure pertains from this description.

Therefore, the spirit of the present disclosure should not be limited to these embodiments, but the claims and all of modifications equal or equivalent to the claims are intended to fall within the scope and spirit of the present disclosure.

What is claimed is:

1. An optimization system of an artificial intelligence (AI) algorithm for predicting a lesion in a coronary artery based on a fractional flow reserve (FFR), comprising:
   one or more memories; and
   one or more processors operably coupled with the one or memories, the one or more processors configured to cause:
   collecting preset factor data in order to predict an FFR numerical value;
   analyzing a correlation between the factor data and eliminating specific factor data;
   performing learning processing using the factor data from which the specific factor data have been eliminated processing unit using a plurality of pre-stored AI algorithms, analyze a learning result, and perform optimization processing of each AI algorithm based on an analysis result,
   dividing all of the factor data from which the specific factor data have been eliminated into training data and test data according to a plurality of predetermined ratios to generate a plurality of training data sets; and
   inputting each of the plurality of training data sets into each of the plurality of AI algorithms to perform learning processing such that a plurality of learning result models are generated for each AI algorithm.

2. The optimization system of an AI algorithm for predicting a lesion in a coronary artery based on an FFR of claim 1, wherein the collecting preset factor data includes:

receiving biometric factor data for each patient from the outside;

receiving blood vessel shape factor data generated based on medical image data for each patient from the outside;

generating flow factor data for a cardiovascular region for each patient using the blood vessel shape factor data, and receiving an FFR value measured or predicted for each patient from the outside.

3. The optimization system of an AI algorithm for predicting a lesion in a coronary artery based on an FFR of claim 2, wherein the generating the flow factor data includes:

generating a plurality of virtual blood vessel models in advance, performing a computational fluid dynamics (CFD) simulation for the generated virtual blood vessel models, and constructing a database of CFD simulation performing result data for each virtual blood vessel model to store and manage the CFD simulation performing result data; and deriving performing result data corresponding to the blood vessel shape factor data and generating the performing result data as the flow factor data.

4. The optimization system of an AI algorithm for predicting a lesion in a coronary artery based on an FFR of claim 2, wherein the analyzing a correlation between the factor data and eliminating specific factor data includes:

constructing a database of the biometric factor data, the blood vessel shape factor data, and the flow factor data by the data collection unit for each patient;

analyzing a correlation between each factor data and the received FFR value by applying a pre-stored technique;

selecting specific factor data of which a correlation is a predetermined reference or less based on an analysis result by applying a pre-stored technique and eliminate all factor data of a corresponding patient including the specific factor data; and correcting and reconstructing the database by the DB construction unit based on an elimination result.

5. The optimization system of an AI algorithm for predicting a lesion in a coronary artery based on an FFR of claim 4, wherein the performing learning processing includes:

performing learning processing by inputting the database as the training data to a plurality of pre-stored heterogeneous AI algorithms; and receiving an FFR prediction result using a learning result model for each AI algorithm and analyzing prediction result accuracy for each learning result model, wherein the performing learning processing by inputting the database includes dividing all the factor data included in the database into the training data and the test data according to the plurality of predetermined ratios by applying a pre-stored technique to generate the plurality of training data sets, and then inputting each of the plurality of training data sets into each AI algorithm to perform learning processing, and wherein the receiving an FFR prediction result includes analyzing accuracy of an FFR prediction result output from each learning result model using the test data.

6. The optimization system of an AI algorithm for predicting a lesion in a coronary artery based on an FFR of claim 5, wherein the receiving an FFR prediction result includes analyzing the accuracy of the FFR prediction result output from each learning result model to derive a specific ratio having the highest FFR prediction accuracy for each AI algorithm.

7. The optimization system of an AI algorithm for predicting a lesion in a coronary artery based on an FFR of claim 6, wherein the performing learning processing further includes:

controlling a weight for a hyper parameter that determines a property for each of the plurality of pre-stored heterogeneous AI algorithms by applying a pre-stored technique and inputting the training data divided according to the specific ratio having the highest FFR prediction accuracy first to each controlled AI algorithm to perform learning processing; and receiving an FFR prediction result for each learning result model using the test data divided according to the specific ratio having the highest FFR prediction accuracy and analyzing prediction result accuracy for each learning result model, wherein the controlling a weight for a hyper parameter includes controlling control-weights for corresponding hyper parameters for each AI algorithm plural times under different conditions, and repeatedly performing learning processing for each controlled AI algorithm.

8. The optimization system of an AI algorithm for predicting a lesion in a coronary artery based on an FFR of claim 7, wherein the receiving an FFR prediction result includes extracting a learning result model having the highest FFR prediction accuracy for each AI algorithm, and analyzing a weight control condition of a hyper parameter for the corresponding learning result model.

9. An optimization method of an AI algorithm for predicting a lesion in a coronary artery based on an FFR that uses an optimization system of an AI algorithm for predicting a lesion in a coronary artery based on an FFR performed by a computer, comprising:

collecting preset factor data in order to predict an FFR numerical value;

analyzing a correlation between the factor data and eliminating specific factor data; and inputting the factor data from which the specific factor data have been eliminated to a plurality of pre-stored AI algorithms to perform learning processing, analyzing a learning result, and performing optimization processing of each AI algorithm based on an analysis result, wherein the inputting the factor data comprises:

dividing all of the factor data from which the specific factor data have been eliminated into training data and test data according to a plurality of predetermined ratios to generate a plurality of training data sets; and inputting each of the plurality of training data sets into each of the plurality of AI algorithms to perform learning processing such that a plurality of learning result models are generated for each AI algorithm.

10. The optimization method of an AI algorithm for predicting a lesion in a coronary artery based on an FFR of claim 9, wherein the collecting preset factor data includes:

receiving biometric factor data, blood vessel shape factor data, and a measured or predicted FFR value for each patient; and generating flow factor data for a cardiovascular region for each patient using the blood vessel shape factor data.

11. The optimization method of an AI algorithm for predicting a lesion in a coronary artery based on an FFR of claim 10, wherein the generating flow factor data includes:

generating a plurality of virtual blood vessel models in advance, performing a CFD simulation for the generated virtual blood vessel models, and constructing a database of CFD simulation performing result data for each virtual blood vessel model to store and manage the CFD simulation performing result data; and deriving CFD simulation performing result data corresponding to the blood vessel shape factor data and generating the CFD simulation performing result data as the flow factor data.

12. The optimization method of an AI algorithm for predicting a lesion in a coronary artery based on an FFR of claim 10, wherein the analyzing a correlation between the factor data and eliminating specific factor data includes:

constructing a database of the factor data for each patient;

analyzing a correlation between each factor data and the FFR value by applying a pre-stored technique;

selecting specific factor data of which a correlation is a predetermined reference or less based on an analysis result by applying a pre-stored technique and eliminating all factor data of a corresponding patient including the specific factor data; and correcting and reconstructing the database based on an elimination result.

13. The optimization method of an AI algorithm for predicting a lesion in a coronary artery based on an FFR of claim 12, wherein the inputting the factor data includes:

performing learning processing by inputting the database as training data to a plurality of pre-stored heterogeneous AI algorithms, and dividing all the factor data included in the database into the training data and the test data according to the plurality of predetermined ratios by applying a pre-stored technique to generate the plurality of training data sets and then inputting each of the plurality of training data sets to each AI algorithm; and receiving an FFR prediction result for each learning result model using each test data and the FFR value and analyzing accuracy of each learning result model based on the FFR prediction result, and a specific ratio having the highest FFR prediction accuracy is derived for each AI algorithm.

14. The optimization method of an AI algorithm for predicting a lesion in a coronary artery based on an FFR of claim 13, wherein the inputting the factor data further includes:

controlling weights for hyper parameters that determine a property for each of the plurality of pre-stored heterogeneous AI algorithms plural times under different conditions by applying a pre-stored technique and inputting the training data divided according to the specific ratio having the highest FFR prediction accuracy derived to each controlled AI algorithm to perform learning processing; and receiving an FFR prediction result for each learning result model using the test data divided according to the specific ratio having the highest FFR prediction accuracy derived and the received FFR and analyzing accuracy of each learning result model based on the FFR prediction result, and a learning result model having the highest FFR prediction accuracy for each AI algorithm is extracted, and a weight control condition of a hyper parameter for the corresponding learning result model is analyzed.

* * * * *